(12) United States Patent
Fukuoka et al.

(10) Patent No.: US 10,544,764 B2
(45) Date of Patent: Jan. 28, 2020

(54) FUEL PUMP, FUEL SUPPLY DEVICE, AND FUEL SUPPLY CONTROL SYSTEM

(71) Applicant: DENSO CORPORATION, Kariya, Aichi-pref. (JP)

(72) Inventors: Shingo Fukuoka, Kariya (JP); Kiyoshi Nagata, Kariya (JP); Hiromi Sakai, Kariya (JP); Yuuji Hidaka, Kariya (JP)

(73) Assignee: DENSO CORPORATION, Kariya (JP)

( * ) Notice: Subject to any disclaimer, the term of this patent is extended or adjusted under 35 U.S.C. 154(b) by 66 days.

(21) Appl. No.: 16/069,015

(22) PCT Filed: Jan. 24, 2017

(86) PCT No.: PCT/JP2017/002206
§ 371 (c)(1),
(2) Date: Jul. 10, 2018

(87) PCT Pub. No.: WO2017/138344
PCT Pub. Date: Aug. 17, 2017

(65) Prior Publication Data
US 2019/0017475 A1   Jan. 17, 2019

(30) Foreign Application Priority Data
Feb. 12, 2016  (JP) ................................. 2016-025155

(51) Int. Cl.
*F02M 37/00* (2006.01)
*F02M 37/14* (2006.01)
(Continued)

(52) U.S. Cl.
CPC .......... *F02M 37/14* (2013.01); *F02D 19/084* (2013.01); *F02D 19/087* (2013.01);
(Continued)

(58) Field of Classification Search
CPC ........ F02M 37/10; F02M 37/14; F02M 37/22; F02M 37/44; F02M 2037/085;
(Continued)

(56) References Cited

U.S. PATENT DOCUMENTS

| 4,905,655 A | * | 3/1990 | Maekawa | ........... F02D 19/0684 123/1 A |
| 5,179,926 A | * | 1/1993 | Ament | ................ F02D 41/0025 123/1 A |

(Continued)

FOREIGN PATENT DOCUMENTS

| JP | 2006-322401 | 11/2006 |
| JP | 2008-255907 | 10/2008 |

(Continued)

*Primary Examiner* — Phutthiwat Wongwian
*Assistant Examiner* — Sherman D Manley
(74) *Attorney, Agent, or Firm* — Nixon & Vanderhye PC

(57) ABSTRACT

A fuel pump has a pump function of sucking fuel in a fuel tank and discharging fuel, and a detection function of detecting a capacitance correlated to a concentration of alcohol in fuel in the fuel tank. The fuel pump includes a pump main body that is received in the fuel tank to perform the pump function, a housing electrode that covers the pump main body in the fuel tank, and an outside electrode that is located outside of the housing electrode in the fuel tank. A gap is formed between the outside electrode and the housing electrode to give the capacitance.

6 Claims, 6 Drawing Sheets

(51) Int. Cl.

| | | |
|---|---|---|
| *F02D 19/08* | (2006.01) | |
| *F02M 37/10* | (2006.01) | |
| *F02D 41/00* | (2006.01) | |
| *F02D 41/30* | (2006.01) | |
| *F02M 37/22* | (2019.01) | |
| *G01N 33/28* | (2006.01) | |
| *G01N 27/22* | (2006.01) | |
| *F02M 37/44* | (2019.01) | |
| *F02M 37/08* | (2006.01) | |

(52) U.S. Cl.
CPC ..... *F02D 41/0025* (2013.01); *F02D 41/3082* (2013.01); *F02M 37/10* (2013.01); *F02M 37/22* (2013.01); *G01N 33/2852* (2013.01); *F02D 2200/0611* (2013.01); *F02M 37/44* (2019.01); *F02M 2037/085* (2013.01); *G01N 27/22* (2013.01)

(58) Field of Classification Search
CPC .. F02D 19/084; F02D 19/087; F02D 41/3082; F02D 41/0025; F02D 2200/0611; G01N 33/2852; G01N 27/22
See application file for complete search history.

(56) References Cited

U.S. PATENT DOCUMENTS

| | | | | |
|---|---|---|---|---|
| 5,515,280 | A * | 5/1996 | Suzuki | F02D 41/0025 701/29.2 |
| 6,615,656 | B1 * | 9/2003 | Breed | B60J 10/00 177/136 |
| 2003/0101972 | A1 * | 6/2003 | Burke | G01N 33/2829 123/520 |
| 2003/0213293 | A1 * | 11/2003 | Lee | F02D 19/0628 73/114.39 |
| 2006/0042940 | A1 | 3/2006 | Kawanishi et al. | |
| 2007/0052310 | A1 * | 3/2007 | Sakai | F02M 37/048 310/87 |
| 2009/0193873 | A1 * | 8/2009 | Nakamura | F02D 33/003 73/31.05 |
| 2012/0126835 | A1 * | 5/2012 | Nakamura | G01N 33/2852 324/663 |
| 2012/0248763 | A1 * | 10/2012 | Nakamura | F02D 19/084 285/305 |
| 2013/0257457 | A1 * | 10/2013 | Kato | G01N 33/2852 324/663 |
| 2013/0268209 | A1 * | 10/2013 | Tashima | F02D 41/0025 702/25 |
| 2013/0276532 | A1 * | 10/2013 | Kato | G01F 23/263 73/304 C |
| 2015/0090011 | A1 * | 4/2015 | Kato | G01N 33/2852 73/61.43 |
| 2016/0208747 | A1 * | 7/2016 | Hidaka | F02M 37/10 |

FOREIGN PATENT DOCUMENTS

| | | |
|---|---|---|
| JP | 2010-275909 | 12/2010 |
| JP | 2011-107070 | 6/2011 |
| JP | 2012-163508 | 8/2012 |

* cited by examiner

FUEL PUMP, FUEL SUPPLY DEVICE, AND FUEL SUPPLY CONTROL SYSTEM

This application is the U.S. national phase of International Application No. PCT/JP2017/002206 filed Jan. 24, 2017, which designated the U.S. and claims priority to Japanese Patent Application No. 2016-25155 filed on Feb. 12, 2016, the entire contents of each of which are incorporated herein by reference.

CROSS REFERENCE TO RELATED APPLICATION

This application is based on Japanese Patent Application No. 2016-25155 filed on Feb. 12, 2016, the disclosure of which is incorporated herein by reference.

TECHNICAL FIELD

The present disclosure relates to a fuel pump, a fuel supply device, and a fuel supply control system.

BACKGROUND ART

A fuel pump having a pump function of sucking and discharging fuel in a fuel tank has been widely applied to a fuel supply device and a fuel supply control system. For example, in the fuel supply device, the fuel to be filtered by a filter element in a filter casing in a fuel filter is discharged from the fuel pump before the fuel is filtered, whereby a filtering efficiency can be increased. Further, in the fuel supply control system, the fuel pump is controlled by a control system, whereby a discharge pressure of the fuel can be correctly regulated.

A pump disclosed as a kind of fuel pump like this in Patent Document 1 exerts a pump function and a detection function, thereby detecting a capacitance according to a fuel property in the fuel tank such as an alcohol concentration. Here, in the fuel pump disclosed in Patent Document 1, a fuel property detection device to detect a capacitance correlated to the fuel property forms a gap to give the capacitance between a pair of detection electrodes arranged in a double cylindrical shape.

PRIOR ART DOCUMENT

Patent Document

Patent Document 1: JP 2012-163508A

In the fuel pump disclosed in Patent Document 1, the fuel property detection device constructed of the pair of detection electrodes arranged in the double cylindrical shape is provided externally on the side of the fuel pump. For this reason, in the fuel tank whose volume is limited, a space in which the fuel property detection device is arranged is hard to be secured on the side of the fuel pump. For this reason, a large surface area to form the gap cannot be secured on the respective detection electrodes, which hence results in decreasing a detection accuracy of the capacitance.

SUMMARY OF INVENTION

It is an objective of the present disclosure to provide a fuel pump that detects a capacitance with high accuracy. Further, it is also an objective of the present disclosure to provide a fuel supply device provided with the fuel pump that detects a capacitance with high accuracy. Additionally, it is an objective of the present disclosure to provide a fuel supply control system constructed in such a way as to include the fuel pump that detects a capacitance with high accuracy.

To achieve the objective, a fuel pump in a first aspect of the present disclosure has a pump function of sucking fuel in a fuel tank and discharging fuel, and a detection function of detecting a capacitance correlated to a concentration of alcohol in fuel in the fuel tank. The fuel pump includes a pump main body that is received in the fuel tank to perform the pump function, a housing electrode that covers the pump main body in the fuel tank, and an outside electrode that is located outside of the housing electrode in the fuel tank. A gap is formed between the outside electrode and the housing electrode to give the capacitance.

To achieve the objective, a fuel supply device in a second aspect of the present disclosure includes a fuel pump that has a pump function of sucking fuel in a fuel tank and discharging fuel, and a detection function of detecting a capacitance correlated to a concentration of alcohol in fuel in the fuel tank, and a fuel filter that includes a filter casing and a filter element in the filter casing and filters the fuel discharged by the fuel pump through the filter element. The fuel pump includes a pump main body that is received in the fuel tank to perform the pump function, a housing electrode that covers the pump main body in the fuel tank, and an outside electrode that is located outside of the housing electrode in the fuel tank. A gap is formed between the outside electrode and the housing electrode to give the capacitance. The filter casing includes a holding part that holds the pump main body, and a covering part that covers the outside electrode.

To achieve the objective, a fuel supply control system in a third aspect of the present disclosure includes a fuel pump that has a pump function of sucking fuel in a fuel tank and discharging fuel, and a detection function of detecting a capacitance correlated to a concentration of alcohol in fuel in the fuel tank, and a control system that controls the fuel pump. The fuel pump includes a pump main body that is received in the fuel tank to perform the pump function, a housing electrode that covers the pump main body in the fuel tank, and an outside electrode that is located outside of the housing electrode in the fuel tank. A gap is formed between the outside electrode and the housing electrode to give the capacitance. The control system, which is electrically connected to the housing electrode and the outside electrode, includes an estimation block that estimates the concentration of alcohol based on the capacitance detected by the detection function, and a setting block that sets a pressure of the fuel discharged by the pump function based on the concentration of alcohol estimated by the estimation block.

In the fuel tank in the first to third aspects, the gap which gives the capacitance correlated to the alcohol concentration of the fuel is formed between the housing electrode, which covers the pump main body, and the outside electrode which is located on the outside of the housing electrode. In this way, in the housing electrode and the outside electrode which result in covering the pump main body from the outside, a large surface area of a surface to form the gap can be secured along an outer surface of the pump main body. Hence, a detection accuracy of the capacitance can be increased.

Here, in the second aspect in particular, in the filter casing containing the filter element to filter the discharged fuel from the fuel pump in the fuel filter, the holding part holds the pump main body and the covering part covers the outside electrode. According to this, a relative position of the housing electrode to the outside electrode can be correctly fixed by the use of the filter casing. Hence, fixing the relative position of the housing electrode to the outside electrode in this way can stabilize a size of the gap between the housing electrode and the outside electrode and hence becomes effective for increasing the detection accuracy of the capacitance.

Further, in the third aspect in particular, in the control system electrically connected to the housing electrode and the outside electrode, the estimation block can correctly estimate the alcohol concentration on the basis of the capacitance detected with high accuracy by the detection function of the fuel pump. Hence, in the control system, the pressure of the discharge fuel, which is set by the setting block on the basis of the alcohol concentration correctly estimated, can be inhibited from being shifted from an expected pressure due to a difference in the alcohol concentration. Therefore, also a pressure regulation accuracy of the discharged fuel can be increased.

BRIEF DESCRIPTION OF DRAWINGS

The above and other objects, features and advantages of the present disclosure will become more apparent from the following detailed description made with reference to the accompanying drawings. In the drawings.

EMBODIMENT FOR CARRYING OUT INVENTION

Hereinafter, an embodiment will be described on the basis of the drawings.

Figure 1:
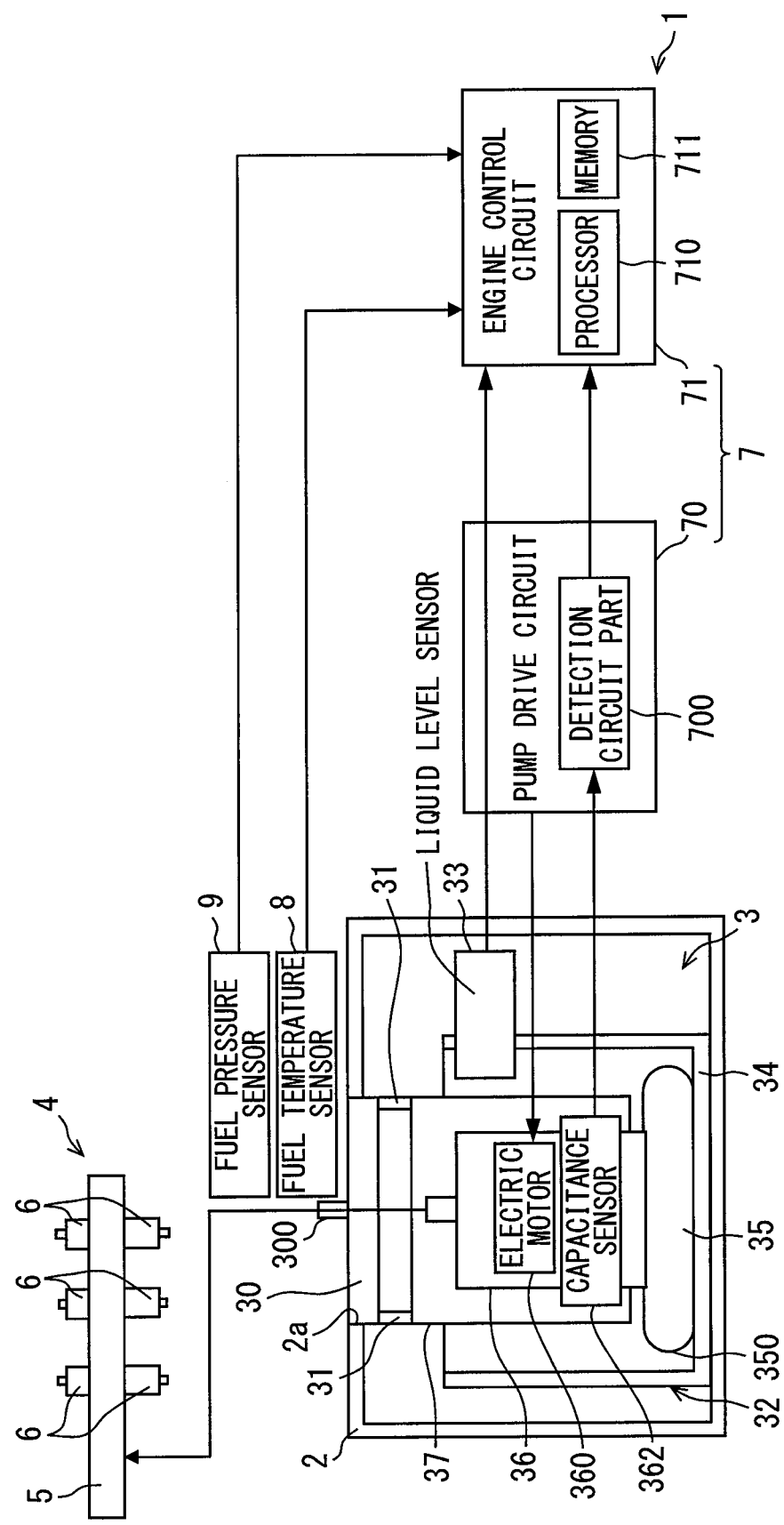
FIG. 1 is a general construction to show a fuel supply control system according to an embodiment.

As shown in FIG. 1, a fuel supply control system 1 mounted in a vehicle in an embodiment controls a fuel supply to an internal combustion engine 4 by a fuel supply device 3 in a fuel tank 2. The fuel supply control system 1 is constructed in such a way as to include the fuel supply device 3 and a control system 7. Here, the fuel tank 2 is formed of resin or metal in a hollow shape and stores fuel. The internal combustion engine 4 injects the fuel, which is supplied to a fuel rail 5 from an interior of the fuel tank 2 by the fuel supply device 3, into a plurality of cylinders from a plurality of fuel injection valves 6 and combusts the fuel. The fuel combusted in the internal combustion engine 4 may be gasoline or light oil and is likely to be mixed with alcohol in either case.

Figure 2:
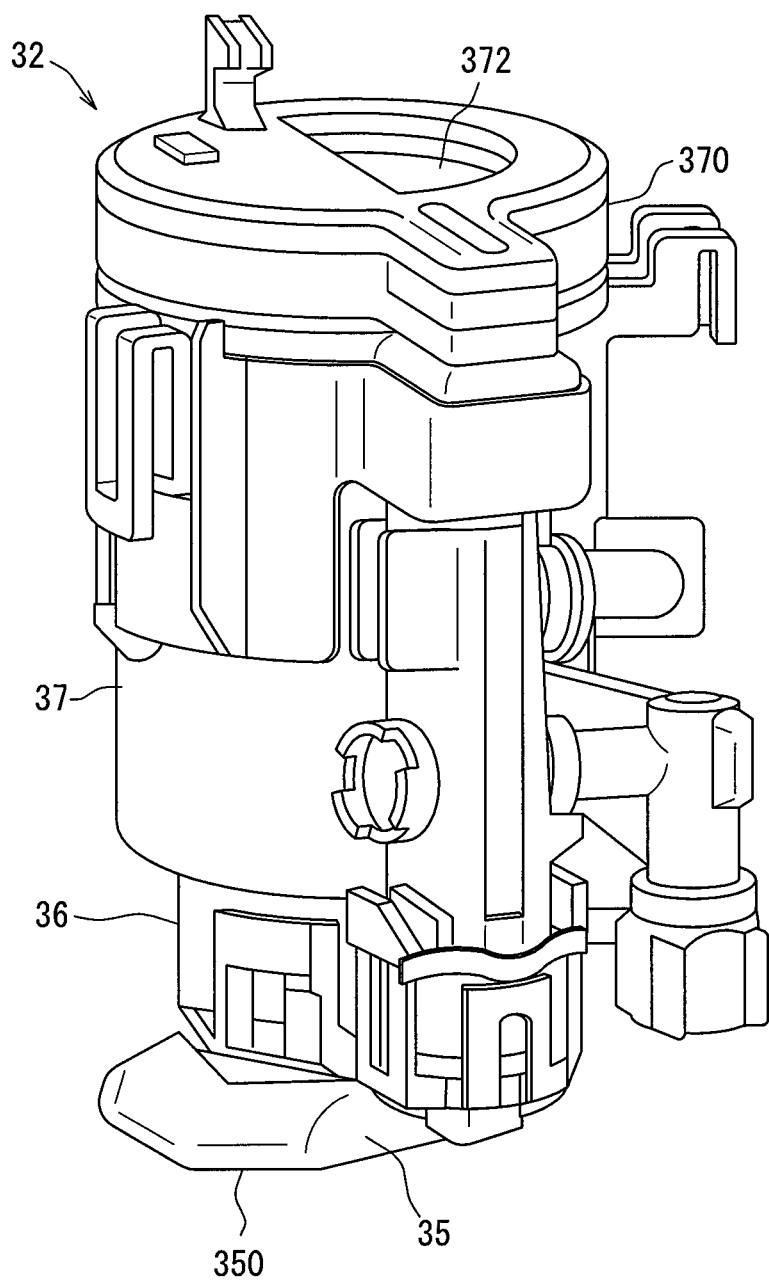
FIG. 2 is a perspective view to show a fuel supply device according to the embodiment.
Figure 3:
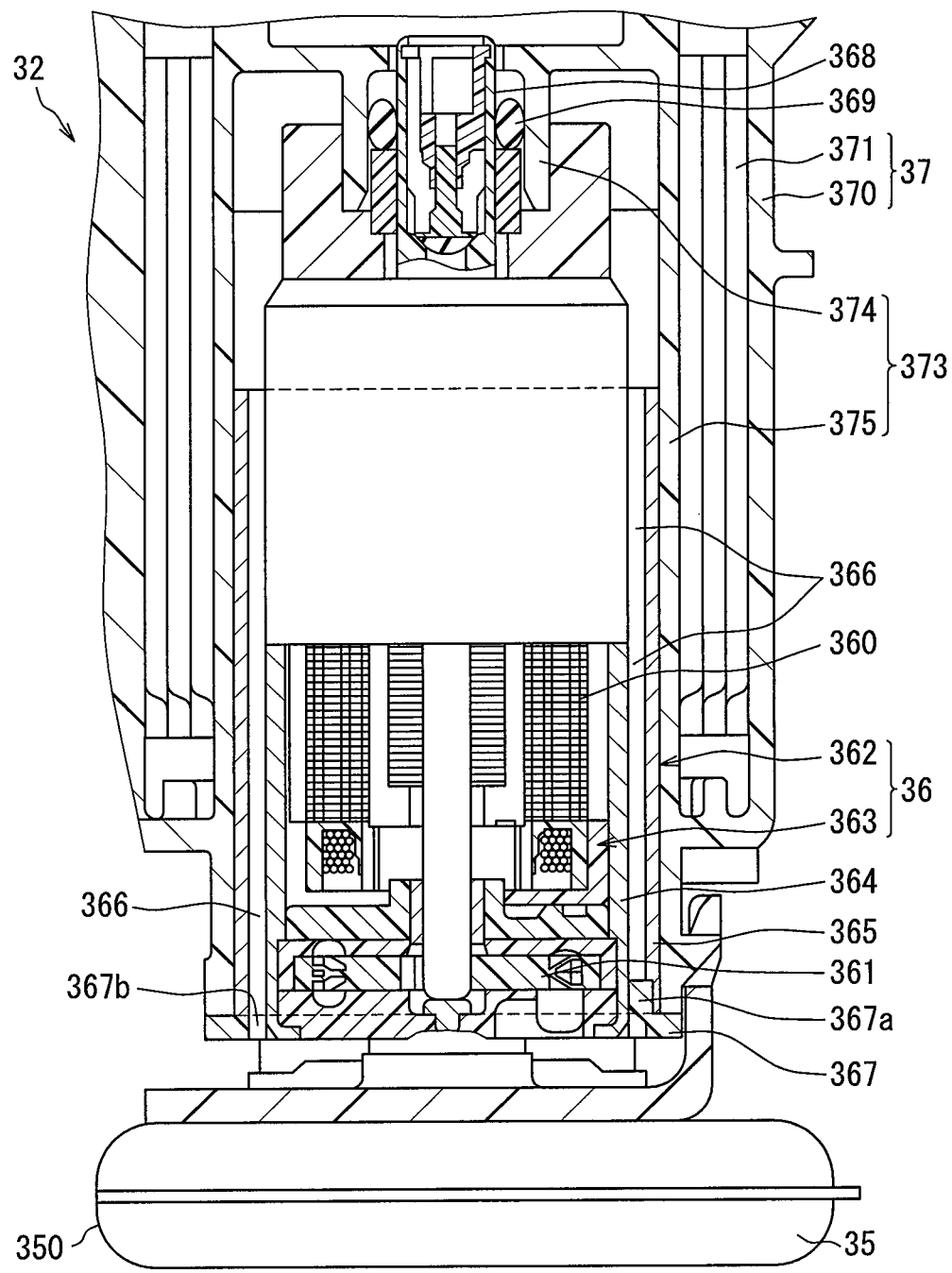
FIG. 3 is a section view, on an enlarged scale, to show the fuel supply device according to the embodiment.

The fuel supply device 3 is provided with a cover 30, a support 31, a pump unit 32, and a liquid level sensor 33. In FIG. 1 and FIGS. 2, 3 which will be described later, an up and down direction of a portion to show the fuel supply device 3 substantially coincides with a vertical direction of the vehicle on a horizontal plane.

As shown in FIG. 1, the cover 30 closes an upper opening 2a of the fuel tank 2. The support 31 is plurally provided. Each of the supports 31 couples the cover 30 and the pump unit 32 in the up and down direction in the fuel tank 2.

The pump unit 32 is received in the fuel tank 2 below the cover 30. A sub-tank 34 of the pump unit 32 is placed on a bottom portion of the fuel tank 2. Fuel flows into the sub-tank 34 from the interior of the fuel tank 2. A suction filter 35, shown in FIGS. 1 to 3, of the pump unit 32 filters the fuel in the sub-tank 34 with a filter element 350 placed on an outer surface thereof, thereby removing a relatively large foreign matter contained in the fuel.

Figure 4:
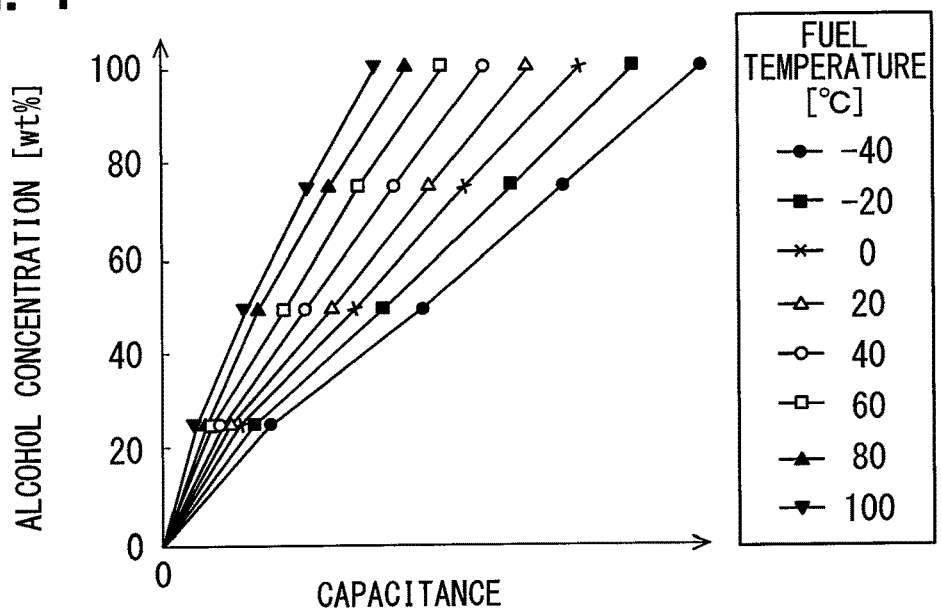
FIG. 4 is a characteristic graph to show a correlation of an alcohol concentration to a capacitance as a characteristic according to the embodiment.

A fuel pump 36 of the pump unit 32 is provided continuously on the suction filter 35. As shown in FIG. 3, the fuel pump 36 is integrally provided with a pump main body 363 and a capacitance sensor 362. The pump main body 363 functions as a so-called impeller type electric pump which rotates an electric motor 360 together with an impeller 361 when voltage is applied to the electric motor 360. The pump main body 363 pressurizes the fuel sucked from an interior of the sub-tank 34 via the suction filter 35 and then discharges the fuel. In a pump function accomplished by the pump main body 363 in this manner, a rotational speed (that is, the number of revolutions per unit time) of each of the electric motor 360 and the impeller 361 can be changed according to an applied voltage, whereby a pressure of a discharged fuel can be regulated. The capacitance sensor 362, as shown in FIG. 4, detects a capacitance correlated to an alcohol concentration.

A fuel filter 37, shown in FIGS. 1 to 3, of the pump unit 32 filters the fuel discharged from the fuel pump 36 by a filter element 371 in a filter casing 370, thereby removing fine foreign matters in the fuel. The fuel filtered by the fuel filter 37 is supplied to the fuel rail 5 through a fuel supply pipe 300 of the cover 30 shown in FIG. 1. The liquid level sensor 33 of the pump unit 32 detects a liquid level of the fuel in the fuel tank 2 and outputs a level signal to indicate a detection level.

As shown in FIG. 1, the control system 7 is provided with a pump drive circuit 70 and an engine control circuit 71.

The pump drive circuit 70 is mainly constructed of a drive IC to drive the electric motor 360 of the fuel pump 36. The pump drive circuit 70 may be placed, for example, in the cover 30 of the fuel supply device 3 in the fuel tank 2 or may be placed outside the fuel tank 2. The pump drive circuit 70 is electrically connected to the electric motor 360 and the engine control circuit 71. The pump drive circuit 70 receives a control signal from the engine control circuit 71. Further, the pump drive circuit 70 sets a target drive voltage in such a way as to realize a target rotational speed to indicate the control signal. Still further, the pump drive circuit 70 controls an actual drive voltage to be applied to the electric motor 360 in such a way that the actual drive voltage becomes the set target drive voltage.

The pump drive circuit 70 is further provided with a detection circuit part 700 which is electrically connected to the capacitance sensor 362 of the fuel pump 36. The detection circuit part 700 applies an alternating current voltage to the capacitance sensor 362, thereby outputting a capacitance signal to indicate a capacitance detected by the capacitance sensor 362 of the fuel pump 36.

The engine control circuit 71 is mainly constructed of a microcomputer including a processor 710 and a memory 711. The engine control circuit 71 is arranged outside the fuel tank 2. Although omitted in the drawing, the engine control circuit 71 is electrically connected to a plurality of electric components such as a fuel injection valve 6 provided in the internal combustion engine 4. The engine control circuit 71 controls actions of these electric components.

The engine control circuit 71 is electrically connected further to the liquid level sensor 33 of the fuel supply device 3, the detection circuit part 700 of the pump drive circuit 70, a fuel temperature sensor 8 and a fuel pressure sensor 9 of the vehicle. Here, in the present embodiment, the liquid level sensor 33 is electrically connected indirectly to the engine control circuit 71 via the pump drive circuit 70. The fuel temperature sensor 8 detects a temperature of the fuel in the fuel tank 2 or a temperature of the fuel discharged from the fuel pump 36 and outputs a fuel temperature signal to indicate a detected temperature. The fuel pressure sensor 9 detects a pressure of the fuel discharged from the fuel pump 36 and outputs a fuel pressure signal to indicate a detected pressure. The fuel temperature sensor 8 and the fuel pressure sensor 9 are electrically connected directly to the engine control circuit 71 or indirectly to the engine control circuit 71 via the pump drive circuit 70.

Figure 5:
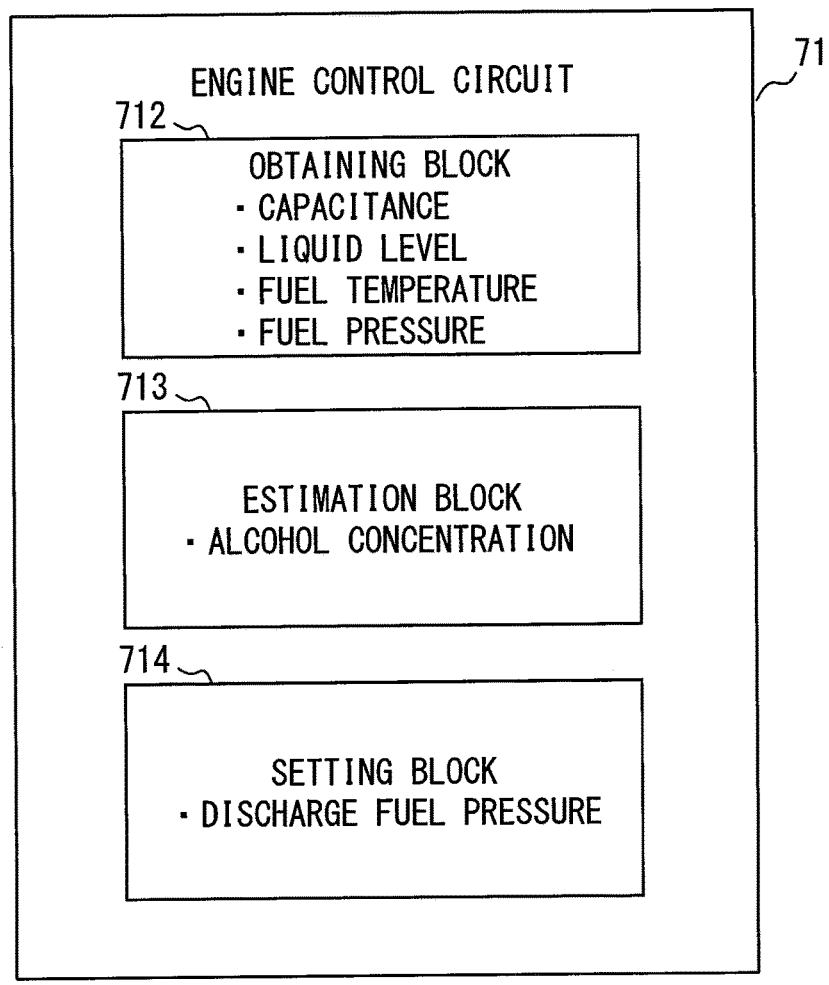
FIG. 5 is a block diagram to show a plurality of blocks which an engine control circuit of a control system according to the embodiment constructs.

The engine control circuit 71 controls an action of the fuel pump 36 on the basis of an output signal from the liquid level sensor 33, the detection circuit part 700, the fuel temperature sensor 8, or the fuel pressure sensor 9 to which the engine control circuit 71 is connected. At this time, the engine control circuit 71 outputs a signal to indicate the target rotational speed of the electric motor 360 as a control signal to be outputted to the pump drive circuit 70 so as to control the action of the fuel pump 36. Here, the engine control circuit 71 of the present embodiment executes a computer program stored in the memory 711 by the processor 710, thereby functionally constructing a plurality of blocks 712, 713, and 714 which are shown in FIG. 5. Of the plurality of blocks 712, 713, and 714, at least a part may be constructed of one IC or a plurality of ICs in a manner of hardware. Further, the memory 711 to memorize a control program or the like to construct the blocks 712, 713, and 714 may be constructed of one storage medium or a plurality of storage media such as a semiconductor memory, a magnetic medium, or an optical medium.

An obtaining block 712 obtains the capacitance, which is detected by a detection function included by the capacitance sensor 362 in the fuel pump 36, on the basis of an output signal from the detection circuit part 700. In addition, the obtaining block 712 obtains the liquid level, the fuel temperature, and the fuel pressure on the basis of the output signal from the sensors 33, 8, and 9.

An estimation block 713 estimates an alcohol concentration in the fuel supplied to the fuel rail 5 from the interior of the fuel tank 2 by the fuel supply device 3. At this time, the estimation block 713 estimates the alcohol concentration on the basis of the capacitance and the fuel temperature obtained by the obtaining block 712. Here, from the fact that a correlation of an alcohol concentration to a capacitance is different with respect to each fuel temperature, as shown in FIG. 4, the alcohol concentration can be correctly estimated. Correlation data stored in the memory 711 in a form of a table, a map, or a function is used as the correlation data to indicate an alcohol concentration with respect to each fuel temperature to a capacitance.

The estimation block 713 of the present embodiment corrects the alcohol concentration, which is estimated in the manner described above, on the basis of the liquid level obtained by the obtaining block 712. At this time, although not shown in the drawing, by utilizing the correlation of the alcohol concentration to the liquid level, the estimation block 713 can correctly correct the alcohol concentration. Correlation data stored in the memory 711 in a form of a table, a map, or a function is used as the correlation data to indicate an alcohol concentration to a liquid level.

As shown in FIG. 5, a setting block 714 sets a pressure of a discharged fuel discharged by a pump function included by the fuel pump 36. At this time, the setting block 714 supposes a vapor amount, which is generated in the discharged fuel due to a mixture of alcohol, on the basis of the fuel temperature obtained by the obtaining block 712 and the alcohol concentration estimated and corrected by the estimation block 713. Further, the setting block 714 sets a pressure of the discharged fuel as a pressure at which the supposed vapor amount can be reduced to an allowable amount or less. Still further, the setting block 714 generates a control signal in such a way that a rotational speed to regulate the fuel pressure, which is obtained by the obtaining block 712, to the pressure of the discharged fuel, which is set by the setting block 714, becomes the target rotational speed of the electric motor 360 in the fuel pump 36. The setting block 714 may set a fuel injection amount from the fuel injection valve 6 and an ignition timing by an ignition coil in each cylinder of the internal combustion engine 4 on the basis of the fuel temperature obtained by the block 712 and the alcohol concentration estimated by the block 713.

Next, a detailed construction of the capacitance sensor 362 provided by the fuel pump 36 will be described. As shown in FIG. 3, the capacitance sensor 362 includes a housing electrode 364, an outside electrode 365, and a spacer 367.

The housing electrode 364 is formed of metal such as a stainless steel or aluminum, which has an electrical conductivity, in a cylindrical shape. A thickness in a radial direction of the housing electrode 364 is set at a substantially constant thickness over the whole circumference. The housing electrode 364 covers the pump main body 363, which is housed in the sub-tank 34 in the fuel tank 2, over the whole circumference from the outside. Here, an electrical insulation is secured between the housing electrode 364 and the pump main body 363 by the use of resin or the like.

The outside electrode 365 is formed of metal such as a carbon steel, which is close to the housing electrode 364 in a point of a corrosion resistance and a fuel resistance and has an electrical conductivity, in a cylindrical shape. A thickness in the radial direction of the outside electrode 365 is set at a substantially constant thickness over the whole circumference. An inside radius of the outside electrode 365 is set larger than an outside diameter of the housing electrode 364. The outside electrode 365 is located on the outside of the housing electrode 364 and coaxially to the housing electrode 364 in the sub-tank 34 in the fuel tank 2, so that the outside electrode 365 and the housing electrode 364 are arranged in a double cylindrical shape. In this way, a gap 366 which has a substantially constant width in the radial direction is formed between the outside electrode 365 and the housing electrode 364 over the whole circumference. Here, in the present embodiment, a length in an axial direction of the outside electrode 365 is set shorter than a length in the axial direction of the housing electrode 364, so that the gap 366 can be secured over the whole length in the axial direction of the outside electrode 365.

The spacer 367 is formed of resin such as polyphenylene sulfide resin or polyacetal resin, which has an electrical insulation, in a shape of a ring. A fitting protruding portion 367a is formed in a protruding shape at one portion or at a plurality of portions separated at equal intervals in a peripheral direction in the spacer 367. The fitting protruding portion 367a is fitted from below in a space between the housing electrode 364 and the outside electrode 365. In this way, the housing electrode 364 and the outside electrode 365 are separated from each other via the fitting protruding portion 367a formed at portions in the peripheral direction, so that the gap 366 having the substantially constant width can be secured between the housing electrode 364 and the outside electrode 365. Here, the fuel in the sub-tank 34 in the fuel tank 2 can flow into the gap 366 from a portion 367b in which the fitting protruding portion 367a is not formed inside the spacer 367. Further, as shown in FIG. 2, the fuel outside the sub-tank 34 in the fuel tank 2 can flow into the gap 366 from an open window 372 which opens in an upper portion of a filter casing 370.

As shown in FIG. 3, the spacer 367 is held by a casing main body 373 containing a filter element 371 of the filter casing 370. The casing main body 373 sandwiches an O ring 369 over the whole circumference between the casing main body 373 and a discharge port 368, from which the fuel is discharged, of the pump main body 363. In this way, the casing main body 373 forms a holding part 374 to hold the pump main body 363 via the O ring 369. In addition, the casing main body 373 is provided with a covering part 375 which covers the whole circumference of the outside electrode 365. Here, the outside electrode 365 in the present embodiment is covered by the covering part 375 by insert resin molding and hence is integrated with the covering part 375, but the outside electrode 365 may be covered by the covering part 375 by fitting or the like.

The housing electrode 364 and the outside electrode 365 are electrically connected individually to the detection circuit part 700 shown in FIG. 1 through an electrical path which couples an interior to an exterior of the fuel tank 2 with a lead wire or a harness. Here, the detection circuit part 700 applies an alternating current voltage between the housing electrode 364 and the outside electrode 365. In this way, a capacitance corresponding to the alcohol concentration in the fuel is given to the gap 366, so that the detection circuit part 700 generates a capacitance signal to indicate the capacitance.

An effect and operation of the present embodiment described up to this point will be described below.

In the fuel tank 2 of the present embodiment, the gap 366 which gives the capacitance correlated to the alcohol concentration of the fuel is formed between the housing electrode 364, which covers the pump main body 363, and the outside electrode 365 which is located on the outside of the housing electrode 364. In this way, in the housing electrode 364 and the outside electrode 365 which result in covering the pump main body 363 from the outside, a large surface area of a surface to form the gap 366 can be secured along an outer surface of the pump main body 363. Hence, the detection accuracy of the capacitance can be increased.

Further, in the fuel filter 37 of the present embodiment, in the filter casing 370 containing the filter element 371 to filter the discharged fuel from the fuel pump 36, the holding part 374 holds the pump main body 363 and the covering part 365 covers the outside electrode 365. According to this construction, a relative position of the housing electrode 364 to the outside electrode 365 can be correctly fixed by the use of the filter casing 370. Hence, fixing the relative position of the housing electrode 364 to the outside electrode 365 in this way can stabilize a size of the gap 366 between the housing electrode 364 and the outside electrode 365 and hence becomes effective for increasing the detection accuracy of the capacitance.

Still further, according to the present embodiment, in the control system 7 electrically connected to the housing electrode 364 and the outside electrode 365, the estimation block 713 can correctly estimate the alcohol concentration on the basis of the capacitance detected with high accuracy by the detection function of the fuel pump 36. Hence, in the control system 7, the pressure of the discharge fuel, which is set by the setting block 714 on the basis of the alcohol concentration correctly estimated, can be inhibited from being shifted from an expected pressure due to a difference in the alcohol concentration. Therefore, also a pressure regulation accuracy of the discharged fuel can be increased.

Still further, according to the present embodiment, the housing electrode 364 and the outside electrode 365 which are arranged in the double cylindrical shape in the fuel tank 2 can expand the surface area of the surface to form the gap 366 as much as possible along a peripheral direction of the double cylindrical shape. Hence, this expansion of the surface area becomes effective for increasing the detection accuracy of the capacitance.

In addition, according to the present embodiment, the width of the gap 366, which can be secured by the fact that the spacer 367 separates the housing electrode 364 from the outside electrode 365, can be stably held. Hence, using the spacer 367 in this manner becomes effective for increasing the detection accuracy of the capacitance.

Up to this point, one embodiment has been described. However, it should not be understood that the present disclosure is limited to the embodiment, but the present disclosure can be applied to various embodiments within a scope not departing from the gist of the present disclosure. Modifications of the embodiment described above will be described below.

Figure 6:
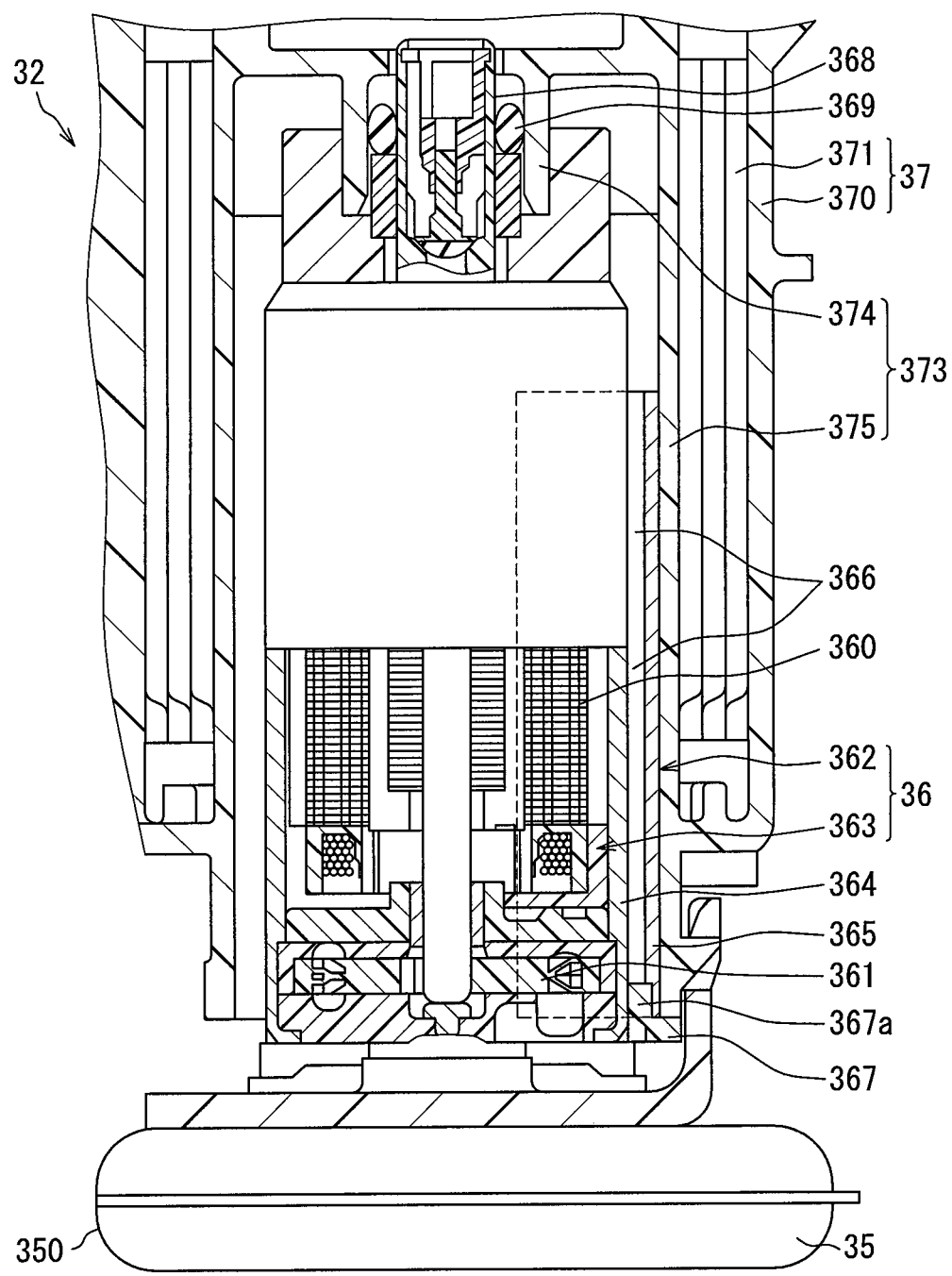
FIG. 6 is a section view to show a modification of FIG. 3.
Figure 7:
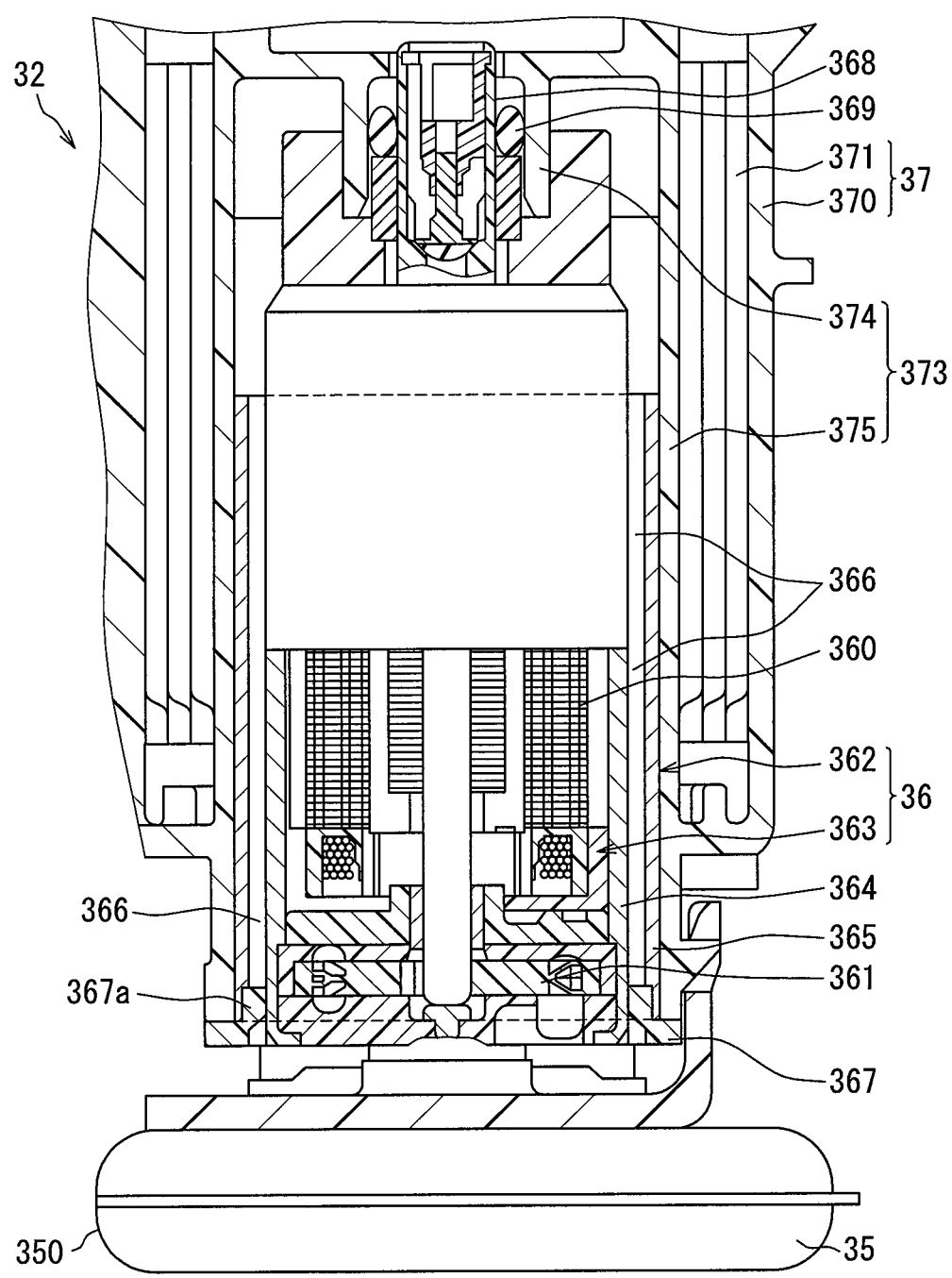
FIG. 7 is a section view to show another modification of FIG. 3.

Specifically, as shown in FIG. 6, as a first modification, the outside electrode 365 formed in an arched plate shape may be arranged on the outside of the housing electrode 364 formed in a cylindrical shape. As shown in FIG. 7, as a second modification, as far as a structure in which the fuel flows into the gap 366 can be secured, the housing electrode 364 and the outside electrode 365 may be separated from each other over the whole circumference by the fitting protruding portion 367a of the spacer 367. As a third modification, the spacer 367 may be not provided. As a fourth modification, the sub-tank 34 may be not provided.

As a fifth modification, the housing electrode 364 may be held by the holding part 374, whereby the pump main body 363 may be held by the holding part 374 indirectly via the housing electrode 364. As a sixth modification, the covering part 375 covering the outside electrode 365 may be not provided on the filter casing 373. As a seventh modification, the pump main body 363 may be a pump other than the impeller type electric pump, for example, a pump functioning as a trochoid type electric pump. As an eighth modification, at least one of the housing electrode 364 and the outside electrode 365 may be formed of a material other than the metal, for example, a conductive resin. As a ninth modification, at least one of the housing electrode 364 and the outside electrode 365 may be formed of a material which does not partially have an electrical conductivity as far as the material can give the capacitance.

As a tenth modification, the estimation block 713 may estimate the alcohol concentration on the basis of the fuel temperature, which is estimated by the control system 7 from a cooling water temperature of the internal combustion engine 4 or from an induced voltage of the electric motor 360, in place of the fuel temperature detected by the fuel temperature sensor 8. As an eleventh modification, in a case where the liquid level is lower than an upper end portion of the gap 366, the estimation block 713 may stop estimating the alcohol concentration in place of correcting the alcohol concentration on the basis of the estimated alcohol concentration. As a twelfth modification, at least one of the blocks 712, 713, 714 may be constructed of the pump drive circuit 70. As a thirteenth modification, the detection circuit part 700 may be provided in the engine control circuit 71 or may be provided outside the pump drive circuit 70 and the engine control circuit 71, for example, in the cover 30.

While the present disclosure has been described with reference to embodiments thereof, it is to be understood that the disclosure is not limited to the embodiments and constructions. The present disclosure is intended to cover various modification and equivalent arrangements. In addition, the various combinations and configurations, other combinations and configurations, including more, less or only a single element, are also within the spirit and scope of the present disclosure.

The invention claimed is:

1. A fuel pump that has:
   a pump function of sucking fuel in a fuel tank and discharging fuel; and
   a detection function of detecting a capacitance correlated to a concentration of alcohol in fuel in the fuel tank, the fuel pump comprising:
   a pump main body that is received in the fuel tank to perform the pump function;
   a housing electrode that covers the pump main body in the fuel tank; and
   an outside electrode that is located outside of the housing electrode in the fuel tank, wherein a gap is formed between the outside electrode and the housing electrode to give the capacitance.

2. The fuel pump according to claim 1, wherein the housing electrode and the outside electrode are arranged in a double-cylindrical shape in the fuel tank.

3. The fuel pump according to claim 1, further comprising a spacer that separates the housing electrode from the outside electrode to secure the gap.

4. The fuel pump according to claim 1, further comprising a filter casing, and a filter element disposed in the filter casing to filter the discharged fuel, wherein:
   the pump main body is held by the filter casing; and
   the outside electrode is covered by the filter casing.

5. A fuel supply device comprising:
   a fuel pump that has:
      a pump function of sucking fuel in a fuel tank and discharging fuel; and
      a detection function of detecting a capacitance correlated to a concentration of alcohol in fuel in the fuel tank; and
   a fuel filter that includes a filter casing and a filter element in the filter casing and filters the fuel discharged by the fuel pump through the filter element, wherein:
   the fuel pump includes:
      a pump main body that is received in the fuel tank to perform the pump function;
      a housing electrode that covers the pump main body in the fuel tank; and
      an outside electrode that is located outside of the housing electrode in the fuel tank;
   a gap is formed between the outside electrode and the housing electrode to give the capacitance; and
   the filter casing includes:
      a holding part that holds the pump main body; and
      a covering part that covers the outside electrode.

6. A fuel supply control system comprising:
   a fuel pump that has:
      a pump function of sucking fuel in a fuel tank and discharging fuel; and
      a detection function of detecting a capacitance correlated to a concentration of alcohol in fuel in the fuel tank; and
   a control system that controls the fuel pump, wherein:
   the fuel pump includes:
      a pump main body that is received in the fuel tank to perform the pump function;
      a housing electrode that covers the pump main body in the fuel tank; and
      an outside electrode that is located outside of the housing electrode in the fuel tank;
   a gap is formed between the outside electrode and the housing electrode to give the capacitance; and
   the control system, which is connected to the housing electrode and the outside electrode, includes:
      an estimation block that estimates the concentration of alcohol based on the capacitance detected by the detection function; and
      a setting block that sets a pressure of the fuel discharged by the pump function based on the concentration of alcohol estimated by the estimation block.

* * * * *